(12) United States Patent
Kalina et al.

(10) Patent No.: US 7,160,716 B2
(45) Date of Patent: Jan. 9, 2007

(54) DEVICE FOR INDUCING AN IMMUNE RESPONSE IN CANCER THERAPY

(76) Inventors: Vladimir Kalina, Chemin du Devin 94, Lausanne (CH) CH 1012; Pavel Richter, Laskova 1793/21, Praha 4, Chodov (CZ); Vratislav Horak, Pod Kostelickem 251, Libechov (CZ) 27721

( * ) Notice: Subject to any disclaimer, the term of this patent is extended or adjusted under 35 U.S.C. 154(b) by 479 days.

(21) Appl. No.: 10/435,731

(22) Filed: May 9, 2003

(65) Prior Publication Data

US 2004/0147962 A9 Jul. 29, 2004

Related U.S. Application Data

(63) Continuation-in-part of application No. PCT/CZ01/00072, filed on Dec. 10, 2001.

(30) Foreign Application Priority Data

Jan. 18, 2001 (CZ) .................................. 2001-232

(51) Int. Cl.
*C12M 1/00* (2006.01)
*C12M 1/12* (2006.01)
*A61K 39/00* (2006.01)
*C12N 11/04* (2006.01)
*C12N 5/06* (2006.01)
*C12N 5/08* (2006.01)
*A01N 1/02* (2006.01)

(52) U.S. Cl. .............................. 435/283.1; 424/184.1; 424/423; 435/182; 435/284.1; 435/297.1; 435/325

(58) Field of Classification Search ..................... None
See application file for complete search history.

(56) References Cited

U.S. PATENT DOCUMENTS

| 4,892,538 | A | | 1/1990 | Aebischer et al. ........ 604/891.1 |
|-----------|---|---|--------|------------------------------------|
| 5,011,472 | A | | 4/1991 | Aebischer et al. ............ 604/50 |
| 5,487,739 | A | | 1/1996 | Aebischer et al. ....... 604/890.1 |
| 5,626,561 | A | * | 5/1997 | Butler et al. ................. 604/500 |
| 5,773,286 | A | | 6/1998 | Dionne et al. ........... 435/297.1 |
| 5,980,889 | A | * | 11/1999 | Butler et al. ............... 424/93.7 |
| 6,179,826 | B1 | | 1/2001 | Aebischer et al. .......... 604/522 |
| 6,797,508 | B1 | * | 9/2004 | Holker .................... 435/252.1 |

FOREIGN PATENT DOCUMENTS

| EP | 0758 553 A2 | 2/1997 |
|----|-------------|--------|
| WO | WO 89/04655 | 6/1989 |
| WO | WO 91/00119 | 1/1991 |
| WO | WO 93/21902 | 1/1993 |

* cited by examiner

*Primary Examiner*—David M. Naff
(74) *Attorney, Agent, or Firm*—Winston & Strawn LLP

(57) ABSTRACT

A device for inducing an immune response in cancer therapy in which isolated living malignant tissue is enclosed in a space formed by a microporous membrane and a holder which is introduced into a body cavity so that macromolecular and cellular immune system components can pass freely in both directions through the membrane while malignant cells of the tumor tissue remain trapped inside.

25 Claims, 2 Drawing Sheets

DEVICE FOR INDUCING AN IMMUNE RESPONSE IN CANCER THERAPY

CROSS-REFERENCE TO RELATED APPLICATIONS

Figure 1:
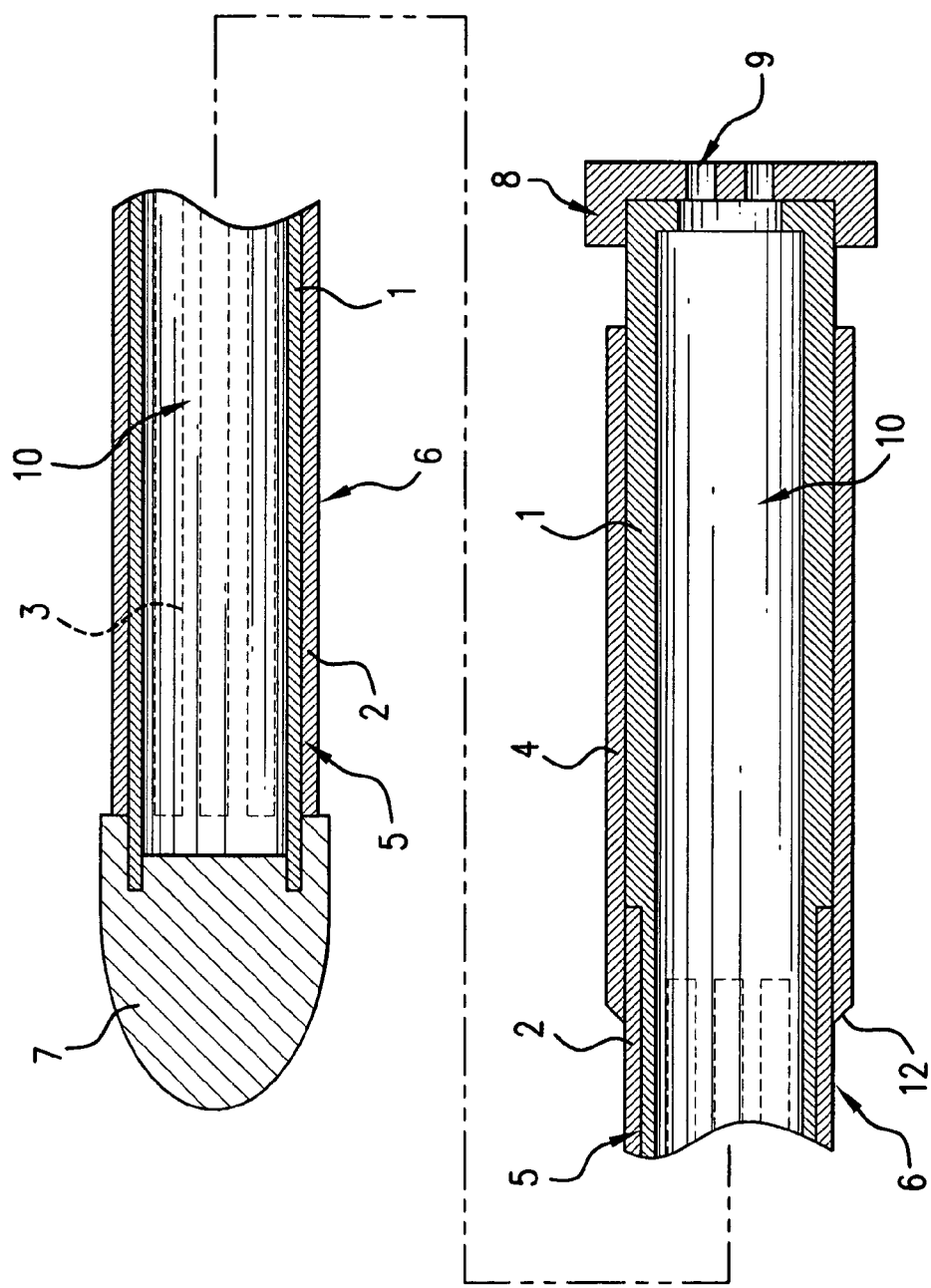

This application is a continuation-in-part of the US National Phase of International Application PCT/CZ01/00072 filed Dec. 10, 2001, the entire content of which is expressly incorporated herein by reference thereto.

FIELD OF THE INVENTION

This invention relates to the use of microporous membranes in which is enclosed isolated living malignant tissue for the purpose of inducing a strong immune response after introduction in a body cavity in the treatment of malignant tumors.

The invention relates especially to the use of artificial membranes, which are not only compatible with the physiological environment in the body but enable the exchange of macromolecular and cellular components of the immune system in both directions without allowing the leakage of malignant cells into the blood and lymphatic circulation (i.e. after introduction of the membrane with the isolated tissue into the body cavity in a suitable holder).

DESCRIPTION OF THE PRIOR ART

A very efficient method in the treatment of cancer is known under the term "devitalization". The devitalization surgical technique has been described extensively in the literature not only in its application in model experiments using animals (Fortyn, K., et al. Z.exp.Chir.Transplant.kunstl. Organe. 18 :34–41, 1985; Fortyn, K. et al. Acta Chirurgica Hungarica. 29 (2) :163–172, 1988) but also in clinical practice particularly in connection with tumor affections of the gastrointestinal tract (Fortyn, K., et al. Klinicka onkologie. 1 : 7–10, 1989).

Devitalization is a surgical intervention which is aimed to interrupt all vascular supply, i.e. simultaneously the arterial flow and venous reflux in a delimited mass of tissue in the body. This stops blood circulation in the affected area, the filtration of serum from the capillaries is brought to a halt and the production of lymph ceases. The ensuing ischaemia affects nerve extremities in the tissue. The transmission of impulses is thus interrupted and the perception of pain in the devitalized site is relieved. The devascularized tissue is gradually resorbed and the process provokes an immune response by which metastases are eliminated.

The critical physiological condition of the devitalization surgical intervention is that it does not lead to the immediate damaging of the integrity of the plasma membrane of cells in the affected tissue. There is no massive necrotic cytolysis typical for ischaemia which is produced by obstruction of arterial flow and generally leads to the liberation of larger quantities of allergens. These penetrate the tissue not only locally but may also enter the blood and lymphatic circulation. Ischaemia under such conditions normally causes undesirable inflammatory reactions but in extreme cases it may even provoke a fatal systemic shock. This is observed especially in various forms of directed embolization which must not be confused with devitalization.

The physiological effect which is produced by devitalization differs from the effect of simple arterial obstruction in that ordinary embolization mainly leads to the interruption of the oxygen supply while other blood components can still penetrate the affected tissue by venous reflux. Because venous blood deprived of oxygen and saturated with carbon dioxide has a lower value pH a greater amount of calcium which is bound to proteins in the blood is liberated. The lowering of the energetic reserve of ATP in cells as a result of ischaemia disrupts the electric potential at the plasma membrane which is necessary for maintaining normal levels of the intracellular concentration of calcium. With the onset of ischaemia and by the continuing supply of nutrients from the venous reflux, calcium enters tissue cells in larger amounts and activates $Ca^{2+}$ dependent phospholipases. This leads to irreversible damage of the plasma membrane resulting in leakage and massive cellular lysis.

In spite of the fact that devitalization involves a more consequent ischaemia, massive necrotic cytolysis is prevented because the affected tissue is not supplied with blood components that could provoke the disruption of the plasma membrane.

Following devitalization, when venous reflux is arrested, the integrity of the plasma membrane is preserved not only in healthy cells but also in the malignant cells of the affected tissue. The determining circumstance for devitalization to exert its therapeutical effect is the high degree of ischaemia and the lack of growth factors which are two important physiological conditions necessary for immune system triggering of apoptosis or programmed cellular death. In such an environment, cellular distress and immune system signals are generated by all forms of leucocytes particularly monocytes and lymphocytes present in the tissue prior to devitalization. On the other hand, in the case of simple embolization, apoptosis is not likely to occur because the depletion of growth factors and an increasing concentration of intracellular calcium which act in opposition will inhibit the mechanisms normally responsible for its triggering. When apoptosis or programmed cellular death is initiated, cellular disintegration is progressive and is genetically controlled in such a way that it does not lead to the liberation of larger amounts of allergens either locally or into the general circulation. Devitalization, therefore, does not provoke an inflammatory reaction which in acute cases may create an adverse physiological environment linked with the risk of necrotic infection. Apoptosis normally leads to the fragmentation of cellular components and these are progressively phagocytised by competent leucocytes especially macrophages. The affected cellular mass is gradually degraded to simple components by specific enzymes and this contributes to the positive stimulation of the entire immune system. Simultaneously, antigens liberated from malignant cells under these conditions begin to be recognized as non-self and the immune system is mobilized to destroy malignancies in the whole body. The activity is due not only to leucocytes which infiltrate the affected area under the effect of chemotaxis but also leucocytes which are present in the tissue prior to the devitalization intervention.

In principle, devitalization as a surgical technique in which devascularized or completely isolated malignant tissue is left in the body can be applied in the treatment of all types of solid tumors in most organs of the body. A certain exception are soft and highly vascularized tissues and those which are surgically inaccessible. A typical example is brain tissue. Another major disadvantage of the standard devitalization technique is the fact that its application is indicated especially in cases where the tumor affection was diagnosed too late to expect complete remission following either radical surgery or any other type of treatment. These are mostly situations when there is important invasion of the malignancy into surrounding tissues, lymph nodes and even other organs. This means that after the devitalization intervention the possible secondary dissemination of malignant cells does not represent any new potential danger for the patient. In this connection, it is therefore necessary to consider the possibility of an eventual slower immune response if the intervention is carried out at an earlier stage of the tumor affection when it is not possible to predict the reaction of the organism. In such a case, a larger mass of isolated malignant tissue left in a body cavity can be linked with the risk of a more important dissemination of malignant cells even before the immune system is fully mobilized to react and with no possibility of clinically monitoring the progress of the intervention and interrupting it without serious consequences should there be any anomalous behavior.

SUMMARY OF THE INVENTION

The invention relates to a device for inducing a generalized immune response against primary solid rumors and metastases in cancer therapy. This device acts by enclosing autologous live malignant tissue in an inhibitive ischemic environment Conned by a porous membrane supported by a holder which can rake any suitable anatomically compatible shape when introduced either partially or integrally at an implantation site in a body cavity. The membrane generally has pores larger than 2 microns but smaller than the mean size of the cells of the biological tissue which is enclosed in the holder. Thus, the size of the pores is specifically chosen so that all forms of large immunologically active leucocytes can pass freely in and out of the holder while smaller malignant cells of specific tumors remain safely trapped inside without the risk of their secondary dissemination at the implantation site. Preferably; the size of the pores of the membrane ranges from about 6–15 microns.

The holder is generally provided with a tubular shape and is equipped with a cutting member at its inner extremity to cut away fibrous tissue overgrowing the membrane during clinical application of the device. The cutting member of the holder is conveniently designed as a sliding tube or ring possessing a sharp edge. Also, the holder can include tubular extensions for the sampling of biological material during clinical application of the device.

The holder advantageously includes electrodes for the control of physiological factors, such as internal and external temperature. Also, the holder can include an electrode for the control of pH, an electrode for the control of the redox potential, or an electrode for the control of pO2. The holder also can include bioelectrodes, or a heating element. The membrane is preferably made from a hydrophilic plastic material that is compatible with the physiological environment of the body cavity.

Another embodiment of the invention relates to a method for inducing an immune response against malignant cells and tumors in cancer therapy, which comprises enclosing living malignant biological tissue in a space formed by a microporous membrane inside a holder which is introduced either partially or integrally into a body cavity. Any of the holders described herein can be used in this method.

The holder generally has the form of an endoscopic tube which is introduced into the body cavity for a defined period and then removed without the need of a more important surgical intervention. Also, holder may be provided with a flexible extension for integral introduction into the body on the principle of an endoscope. For convenience, the holder may be provided with openings for sampling needles and electrodes.

BRIEF DESCRIPTION OF THE DRAWING FIGURES

Figure 2:
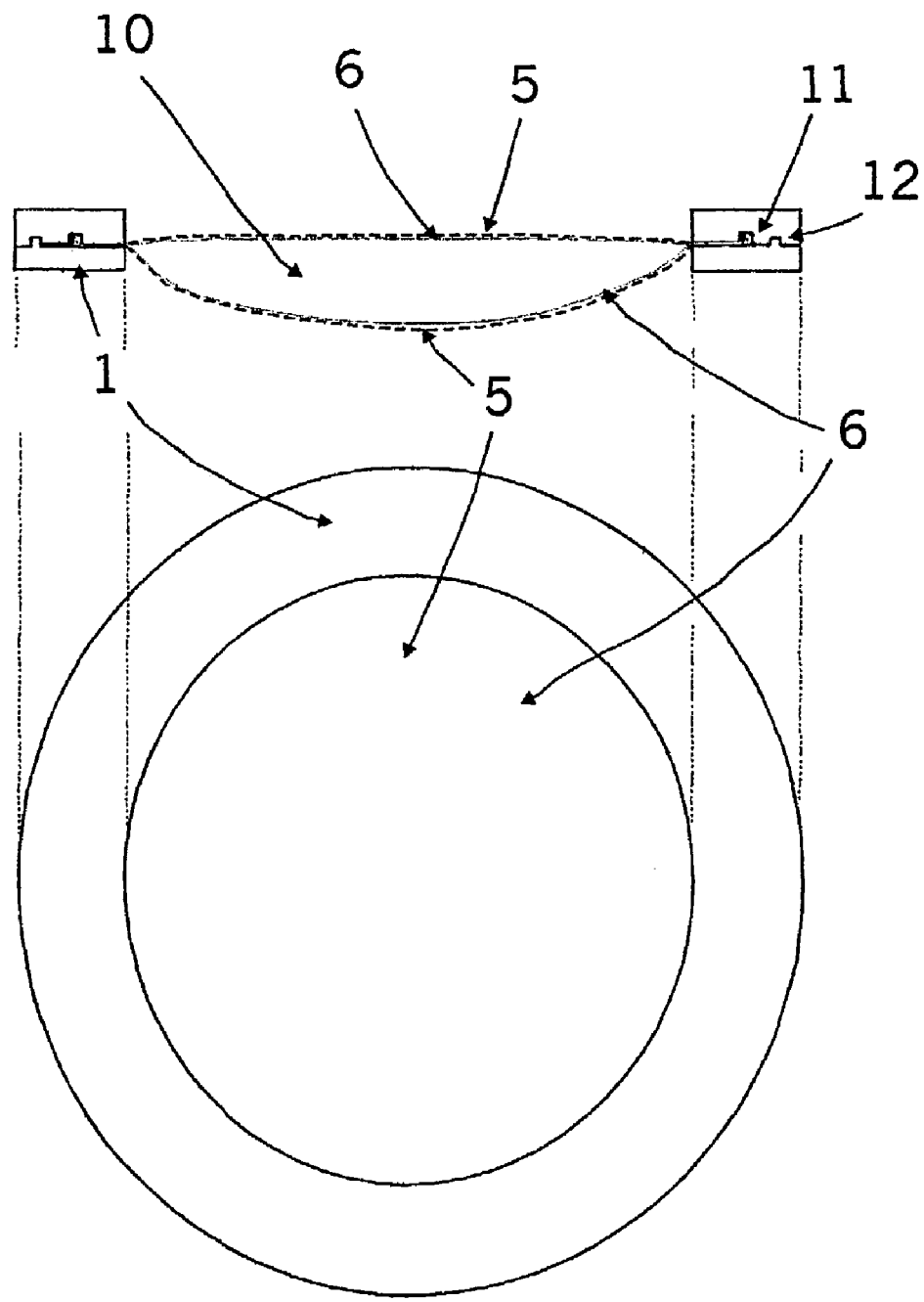

Other features and advantages of the invention will become apparent from the following description in conjunction with the accompanying drawings provided solely by way of example, wherein FIG. 1 is an illustration of a first embodiment of the device of the invention in the form of an universal endoscopic type of device which is particularly suitable for research, and FIG. 2 is an illustration of a second embodiment of the device of the invention wherein the device is introduced into the body by a more invasive operation.

DETAILED DESCRIPTION OF THE INVENTION

The limitations and disadvantages of the standard devitalization surgical technique are for the greater part eliminated by the present invention according to which isolated living malignant tissue, before being introduced into a body cavity, is enclosed in a form of sheath the external part of which is delimited by a microporous membrane. The porous material allows the passage of all molecular and cellular components of the immune system in both directions but not the leakage of malignant cells into the external environment. The device according to this invention is thus open to all processes and physiological mechanisms which are normally induced by the standard devitalization technique but does not allow the secondary dissemination of malignant cells particularly in the case of the devitalization of soft tissues. When using the device according to the present invention malignant tissue can be taken from any part of the body and introduced into any body cavity. The present invention can typically be described as an implantable securized autologous tissue anti-tumor immunization device.

The sheath which encloses the isolated malignant tissue can easily be removed from the body in case of clinical necessity. The device according to the invention allows the systematic sampling of disintegrating tissue material in the course of therapy as well as any type of continuous remote monitoring of physiological parameters. By placing microelectrodes inside the sheath it is possible to monitor temperature, pH, redox potential, $pO_2$ and $pCO_2$ levels. It is recognized that immune response mechanisms are activated by increased temperatures. It is evident, therefore, that the monitoring of temperature offers the possibility of its independent regulation in the tissue which is enclosed in the device. Overall immune response in the body can thus be enhanced. Similarly, with the use of specific bioelectrodes it is possible to monitor continuously the levels of substances linked with the ongoing biological process. The device according to the invention is therefore suitable for research purposes.

The sheath or holder of the device according to the present invention can be constructed in the form of a cylinder, ellipsoid, annulus, or any shape which will assure good harmless anatomical contact of the microporous material with surrounding tissues in the body cavity. The most suitable shape is typical for endoscopic instruments and allows easy introduction through a small opening in the body. An opening in the holder allows the introduction of biological material. It can be closed by a bayonet, screw, watch type fitting or any other suitable mechanism. According to the form of execution the holder is provided with openings for the introduction of hollow sampling needles or the fixation of microelectrodes.

In the construction of the holder it is necessary to use suitable materials which are biologically safe and do not provoke undesirable immune reactions. The holder can be made of all materials which are used successfully in orthopaedic surgery in the various types of prostheses. Such materials are found among stainless steels with a higher content of cobalt, titanium, or metals otherwise used in medicine such as platinum, palladium, gold and other precious metals of group VIII of the periodic system and their alloys. Suitable construction materials are also to be found among plastics based on polyamide, polycarbonate, polyurethane, teflon as well as many others used in surgery (e.g., materials used in the fabrication of artificial heart valves).

The next integral part of the device according to the present invention is the microporous membrane. Products generated by the disintegrating and decomposing devitalized tissue leak out through the microporous membrane filter while macromolecular and cellular components of the immune system pass both in and out. The size of the pores of the membrane fabric is so chosen that leucocytes or lymphocytes which can squeeze through interstices smaller than the normal size of such cells can pass freely whereas tissue cells, which cannot change their shape adequately, remain trapped inside the membrane space. For this reason the size of the pores is critical. It should be larger than 2 microns but not larger than the mean size of the tissue cells which are introduced into the device. The material from which the membranes are made must meet the same conditions of compatibility with the physiological environment in the body as the material of the holder. Such membrane filters are best made from all types of suitably adapted materials used for sterile filtration of liquids in pharmaceutical and medical practice (e.g. Millipore, Ultrapore, Sefar, Pall-Gelman and other industrially manufactured membrane filters). For example, hydrophilic polyamide Nylaflo Pall-Gelman type belongs to the more suitable materials.

The device according to the present invention is described in more detail in the drawings which picture two typical executions. FIG. 1 describes an universal endoscopic type of device, which is particularly suitable for research. FIG. 2 describes the simplest type of device, which is suitable for routine clinical application. Before use the device is sterilized, preferably by gamma irradiation. In both types of the above mentioned devices according to the present invention the isolated living tissue is introduced into the membrane space which is then filled with sterile physiological solution and the holder is immediately closed with the corresponding fitting. The forward part of the device according to FIG. 1 is then surgically introduced through a small opening into the body cavity. The back part of the device which has no membrane surface is fixed securely on the body. It can eventually be extended by a flexible tube to serve as a sheath for electric connections and sampling tubes. The device is maintained in the body cavity either for a limited observation period or for the whole duration of the therapeutical intervention. In the case of the device according to FIG. 2 the procedure is the same as above, except that the whole assembly is introduced into the body by a more invasive operation. It is fixed in a suitable position on the internal wall by stitching to obtain optimal anatomical contact with the membrane part of the holder and without causing any important spatial hindrance in the body cavity. The device is surgically removed from the body at the end of the intervention according to clinical indications.

FIG. 1 is an illustration of a first embodiment of a device in the form of an universal endoscopic. FIG. 1 is a partial long view of the device, wherein a top portion of FIG. 1 can be joined end-to-end with a bottom portion of FIG. 1, i.e.. the right side of the top portion joins the left-side of the bottom portion. The device according to FIG. 1 consists of a tubular holder 1 and a cylindrical membrane assembly 2. The front part of the tubular holder 1 includes a main tubular casing that is provided with lamellar openings 3 that give access to a surface of the membrane filter 6, a porous membrane. A sliding tube 4 which is tightly mounted on the main tubular casing has a knife or sharp edge 12 at the front extremity which serves to remove fibrous overgrowth on the surface of the membrane during a clinical intervention. The length of the sliding tube 4 is adapted to allow the removal of a fibrous deposit along the whole surface of the membrane filter 6. The cylindrical membrane assembly 2 is slipped on the front part of the main tubular casing when a removable head 7 is removed. The internal surface of the cylindrical membrane assembly 2 consists of a supporting netting 5 made of either metal or plastic fiber or out of a perforated material. The supporting netting 5 is covered with the membrane filter 6, for example, a porous membrane or a finer microporous material, and both are welded together at the extremities on a ring which fits tightly on the tubular holder 1. The cylindrical membrane assembly 2 is fixed in position by means of the removable head 7 which closes an opening usable for the introduction of biological material. The removable head 7 is appropriately rounded to assure safe penetration into a body cavity. A rear cap 8 is provided with openings 9 for electrodes and sampling needles. The cylindrical membrane assembly defines an internal space 10, in which the isolated tissue to be devitalized is introduced.

What is claimed is:

1. A device for inducing a generalized immune response against primary solid rumors and metastases in cancer therapy, the device comprising a tubular holder having closed end portions and sidewall openings covered by a porous membrane that acts by enclosing autologous live malignant tissue in the holder when the holder is introduced into an implantation site in a body cavity, wherein the porous membrane has pores larger than 2 microns but smaller than a mean size of cells of the autologous live malignant tissue enclosed in the holder and wherein the size of the pores is specifically chosen so that all forms of large immunologically active leucocytes can pass freely in and out of the holder while smaller cells of the malignant tissue remain safely trapped inside the holder without risk of secondary dissemination at the implantation site.

2. The device according to claim 1, wherein the size of the pores of the membrane is from about 6–15 microns.

3. The device according to claim 1, further comprising a tubular shaped cutting member disposed outside the membrane, to cut away fibrous tissue overgrowing the membrane during clinical application of the device.

4. The device according to claim 3, wherein the cutting member of the holder is a sliding tube possessing a sharp edge.

5. The device according to claim 1, wherein the holder includes tubular extensions for the sampling of biological material during clinical application of the device.

6. The device according to claim 1, wherein the holder includes electrodes for the control of physiological factors.

7. The device according to claim 6, wherein the physiological factors include internal and external temperatures as measured inside and outside of the holder.

8. The device according to claim 1, wherein the holder includes an electrode for the control of pH.

9. The device according to claim 1, wherein the holder includes an electrode for the control of the redox potential.

10. The device according to claim 1, wherein the holder includes an electrode for the control of pCO2.

11. The device according to claim 1, wherein the holder includes bioelectrodes.

12. The device according to claim 1, wherein the membrane is made from a hydrophilic plastic material.

13. The device according to claim 1, wherein the holder is provided with a heating element.

14. The device according to claim 1 wherein one end portion of the holder is a cap that serves as a sheath for sampling and electrical connections.

15. The device according to claim 1 wherein the holder is configured and dimensioned to be introduced into the body cavity for a defined period and then removed without a need of a surgical intervention.

16. The device according to claim 1 wherein the holder includes an electrode for the control of pO2.

17. The device according to claim 1, wherein the device further comprises a netting to support the porous membrane.

18. A device for inducing a generalized immune response against primary solid tumors and metastases for cancer therapy, the device comprising a ring-shaped holder clamping first and second porous membrane portions to define a interior space between the membrane portions the acts by enclosing autologous live malignant tissue wherein the holder is adapted to be introduced into a body cavity, wherein the first and second porous membrane portions have pores that are larger than 2 microns but smaller than a mean size of cells of the autologous live malignant tissue enclosed in the interior space and wherein the size of the pores is specifically chosen so that all forms of immununologically active leucocytes can pass freely in and out of the interior space while smaller cell of the malignant tissue remain safely trapped inside the interior space.

19. The device according to claim 18, wherein the device is provided with electrodes for the control of physiological factors including internal and external temperature as measured inside and outside of the device.

20. The device according to claim 18, wherein the device is provided with an electrode for the control of pH.

21. The device according to claim 18, wherein the device is provided with an electrode for the control of the redox potential.

22. The device according to claim 18, wherein the device is provided with an electrode for the control of $pO_2$.

23. The device according to claim 18, wherein the device is provided with an electrode for the control of $pCO_2$.

24. The device according to claim 18, wherein the holder is provided with a heating element or bioelectrodes.

25. The device according to claim 18, further comprising a netting portion to support the porous membrane portions and the membrane portions are made from a hydrophilic plastic material.

* * * * *

UNITED STATES PATENT AND TRADEMARK OFFICE
CERTIFICATE OF CORRECTION

PATENT NO.        : 7,160,716 B2
APPLICATION NO.   : 10/435731
DATED             : January 9, 2007
INVENTOR(S)       : Kalina et al.

It is certified that error appears in the above-identified patent and that said Letters Patent is hereby corrected as shown below:

Column 3:
Line 20, after "ized immune response against primary solid", delete "rumors" and insert -- tumors --.
Line 23, after "environment", delete "Conned" and insert -- formed --.
Line 24, after "holder which can", delete "rake" and insert -- take --.
Line 34, after "the implantation site." change "Preferably;" to -- Preferably, --.

Column 6:
Line 4, after "be joined end-to-end with a bottom portion of FIG. 1," change "i.e.." to -- i.e., --.
Line 34, before the paragraph "What is claimed is:", insert the following paragraph:
    -- Figure 2 is an illustration of a second embodiment of a device of the invention wherein the device is introduced into a body by a more invasive operation. The device according to Figure 2 consists of two flat rings which together form a clamping holder 1 for first and second portions 5 of a supporting or covering netting and the membrane filter in the form of first and second membrane portions 6, for example, a porous membrane or a fine microporous membrane. This assembly creates the interior space 10 between the membrane portions into which is introduced the isolated tissue to be devitalized. One of the clamping rings is provided with a groove 11 for fitting an O-ring seal. The holder rings are provided with either a ridge or a groove near the external circumference 12 for the purpose of clamping. One of the holder rings is provided with eyehole loops along the circumference for fixing the device on an internal wall of the body or a body cavity. --.

UNITED STATES PATENT AND TRADEMARK OFFICE
CERTIFICATE OF CORRECTION

PATENT NO.       : 7,160,716 B2                                      Page 2 of 2
APPLICATION NO.  : 10/435731
DATED            : January 9, 2007
INVENTOR(S)      : Kalina et al.

It is certified that error appears in the above-identified patent and that said Letters Patent is hereby corrected as shown below:

<u>Column 7:</u>
Line 29 (claim 18, line 6), after "enclosing autologous live malignant", change "tissue" to --tissue,--.

Signed and Sealed this

Sixth Day of March, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,160,716 B2 | Page 1 of 1 |
| APPLICATION NO. | : 10/435731 | |
| DATED | : January 9, 2007 | |
| INVENTOR(S) | : Kalina et al. | |

It is certified that error appears in the above-identified patent and that said Letters Patent is hereby corrected as shown below:

<u>Column 8</u>:
Line 5 (claim 18, line 12), after "specifically chosen so that all forms of", delete "immununologically" and insert -- immunologically --.
Line 7 (claim 18, line 14), after "space while smaller", change "cell" to -- cells --.
Line 22 (claim 24, line 1), after "The device according to claim 18, wherein the", delete "holder" and insert -- device --.

Signed and Sealed this

Thirty-first Day of July, 2007

JON W. DUDAS
*Director of the United States Patent and Trademark Office*